(12) United States Patent
Oien et al.

(10) Patent No.: US 9,629,701 B2
(45) Date of Patent: Apr. 25, 2017

(54) METHOD AND APPARATUS FOR CLEANING AND STORING ENDODONTIC TOOLS

(75) Inventors: Hal J. Oien, Tualatin, OR (US); James B. Johnsen, Beaverton, OR (US)

(73) Assignee: Jordco, Inc., Beaverton, OR (US)

( * ) Notice: Subject to any disclaimer, the term of this patent is extended or adjusted under 35 U.S.C. 154(b) by 1209 days.

(21) Appl. No.: 13/601,855

(22) Filed: Aug. 31, 2012

(65) Prior Publication Data

US 2013/0059266 A1   Mar. 7, 2013

Related U.S. Application Data

(60) Provisional application No. 61/529,653, filed on Aug. 31, 2011, provisional application No. 61/695,227, filed on Aug. 30, 2012.

(51) Int. Cl.
*A61C 19/00* (2006.01)
*A61C 5/44* (2017.01)

(52) U.S. Cl.
CPC .............. *A61C 19/002* (2013.01); *A61C 5/44* (2017.02)

(58) Field of Classification Search
CPC A47L 25/00; A61C 3/00; A61C 5/025; A61C 19/002
See application file for complete search history.

(56) References Cited

U.S. PATENT DOCUMENTS

| | | |
|---|---|---|
| 199,040 A | 1/1878 | Doak |
| 538,482 A | 4/1895 | Doan et al. |
| 574,031 A | 12/1896 | Hakins |
| 711,340 A | 10/1902 | Paynter |
| 745,833 A | 12/1903 | Hanson |
| 750,574 A | 1/1904 | Bicket |
| 810,292 A | 1/1906 | Meaker et al. |
| 895,124 A | 8/1908 | Sundee |
| 897,822 A | 9/1908 | Dougherty |
| 902,109 A | 10/1908 | Powell |
| 983,993 A | 2/1911 | Graef |
| 1,104,650 A | 7/1914 | Fries |
| 1,281,025 A | 10/1918 | Klein |
| 1,287,926 A | 12/1918 | Ecaubert |
| 1,357,063 A | 10/1920 | Korb |

(Continued)

FOREIGN PATENT DOCUMENTS

| | | |
|---|---|---|
| DE | 672565 C | 3/1939 |
| FR | 819512 A | 10/1937 |

OTHER PUBLICATIONS

Mar. 4, 2014, International Preliminary Report on Patentability from the International Bureau of WIPO, in PCT/US2012/053529, which is the international application to this U.S. application.

(Continued)

*Primary Examiner* — Randall Chin
(74) *Attorney, Agent, or Firm* — Kolisch Hartwell, P.C.

(57) ABSTRACT

An endodontic instrument servicing system may comprise a socket-forming member that may include spaced wall members that define a socket. An at least partially open-cell foam body may be secured within the socket that is configured for cleaning contaminated instruments. The body may have an indentation force deflection greater than 120 pounds force (lbf) and be configured to substantially grip a rotating contaminated instrument in contact with the body without tearing the foam body.

10 Claims, 5 Drawing Sheets

(56) References Cited

U.S. PATENT DOCUMENTS

| | | |
|---|---|---|
| 2,058,340 A | 10/1936 | Miller |
| 2,166,835 A | 7/1939 | Yancey |
| 2,222,741 A | 11/1940 | Bush |
| 2,286,292 A | 6/1942 | Mall |
| 2,294,186 A | 8/1942 | Kirschbaum |
| 2,340,024 A | 1/1944 | Skaller |
| 2,371,686 A | 3/1945 | Gaulke |
| 2,394,882 A | 2/1946 | Weyland |
| 2,398,664 A | 4/1946 | Paul |
| 2,479,710 A | 8/1949 | Arnold |
| 2,488,492 A | 11/1949 | Dumbleton |
| 2,539,940 A | 1/1951 | Abramson |
| 2,637,148 A | 5/1953 | Tingvatine |
| 2,645,013 A | 7/1953 | Mathison |
| 2,665,479 A | 1/1954 | Weldon |
| 2,681,772 A | 6/1954 | Charney |
| 2,707,782 A | 5/1955 | Eby |
| 2,873,901 A | 2/1959 | Liniger |
| 2,929,541 A | 3/1960 | Castelli et al. |
| 2,942,764 A | 6/1960 | Castelli |
| 2,967,651 A | 1/1961 | Zackheim et al. |
| 2,971,637 A | 2/1961 | Simons |
| 3,016,639 A | 1/1962 | Kennedy et al. |
| 3,071,299 A | 1/1963 | Brown |
| 3,072,244 A | 1/1963 | Smith |
| 3,081,475 A | 3/1963 | Vosbikian et al. |
| 3,092,443 A | 6/1963 | Dietz |
| 3,107,832 A | 10/1963 | Kotkins |
| 3,136,462 A | 6/1964 | Knutson |
| 3,246,815 A | 4/1966 | Aronson |
| 3,265,264 A | 8/1966 | Stephens |
| 3,275,329 A | 9/1966 | Lieberman et al. |
| 3,327,391 A | 6/1967 | Malm |
| 3,331,868 A | 7/1967 | Holden et al. |
| 3,421,679 A | 1/1969 | Goldman |
| 3,473,991 A | 10/1969 | Ludwig |
| 3,503,397 A | 3/1970 | Fogarty et al. |
| 3,530,979 A | 9/1970 | Merrill, Jr. et al. |
| 3,579,306 A | 5/1971 | Crane |
| 3,696,916 A | 10/1972 | Penniman et al. |
| 3,739,420 A | 6/1973 | Kafkis |
| 3,777,882 A | 12/1973 | McIntyre |
| 3,783,996 A | 1/1974 | Gerard et al. |
| 3,857,133 A | 12/1974 | Linenfelser |
| 3,881,868 A | 5/1975 | Duke |
| 3,933,286 A | 1/1976 | Karkas |
| 3,949,568 A | 4/1976 | Gallagher |
| 4,026,063 A | 5/1977 | Allen et al. |
| 4,027,410 A | 6/1977 | Wheeler |
| 4,079,530 A | 3/1978 | Atherton et al. |
| 4,136,773 A | 1/1979 | Booth |
| 4,191,291 A | 3/1980 | Brown |
| D256,999 S | 9/1980 | Haagedoorn et al. |
| 4,232,784 A | 11/1980 | Hesselgren |
| 4,251,482 A | 2/1981 | Sanderson et al. |
| 4,253,830 A | 3/1981 | Kazen et al. |
| 4,280,808 A | 7/1981 | Johnsen et al. |
| 4,306,862 A | 12/1981 | Knox |
| 4,349,632 A | 9/1982 | Lyman et al. |
| 4,375,863 A | 3/1983 | Kappler |
| 4,397,395 A | 8/1983 | McKelvey |
| 4,402,407 A | 9/1983 | Maly |
| 4,427,130 A | 1/1984 | Szigeti |
| 4,502,485 A | 3/1985 | Burgin |
| 4,503,972 A | 3/1985 | Nelligan et al. |
| 4,506,404 A | 3/1985 | Clay |
| 4,512,471 A | 4/1985 | Kaster et al. |
| 4,609,126 A | 9/1986 | Janda |
| 4,634,077 A | 1/1987 | Wilson |
| 4,643,674 A | 2/1987 | Zdarsky |
| 4,661,326 A | 4/1987 | Schainholz |
| 4,694,956 A | 9/1987 | Sims |
| 4,698,210 A | 10/1987 | Solazzi |
| 4,706,839 A | 11/1987 | Spence |
| 4,717,057 A | 1/1988 | Porteous |
| 4,726,470 A | 2/1988 | Lieberman |
| 4,762,247 A | 8/1988 | Temmesfeld |
| 4,772,201 A | 9/1988 | Johnsen et al. |
| 4,822,280 A | 4/1989 | Rider |
| 4,844,308 A | 7/1989 | Porteous |
| 4,859,423 A | 8/1989 | Perlman |
| 4,867,305 A | 9/1989 | Schneider |
| 4,888,487 A | 12/1989 | Ritter |
| 4,898,276 A | 2/1990 | Georgakis |
| 4,901,847 A | 2/1990 | Kesling |
| 4,925,073 A | 5/1990 | Tarrson et al. |
| 4,960,220 A | 10/1990 | Foa |
| 4,969,226 A | 11/1990 | Seville |
| 4,973,847 A | 11/1990 | Lackey et al. |
| 4,976,615 A | 12/1990 | Kravitz |
| 4,991,759 A | 2/1991 | Scharf |
| 5,006,066 A | 4/1991 | Rouse |
| 5,016,795 A | 5/1991 | Porteous |
| 5,029,252 A | 7/1991 | Ameseder |
| 5,054,674 A | 10/1991 | Fortman |
| 5,057,016 A | 10/1991 | Lukase et al. |
| 5,076,437 A | 12/1991 | Schindler |
| 5,106,297 A | 4/1992 | Discko, Jr. |
| 5,108,287 A | 4/1992 | Yee et al. |
| 5,139,188 A | 8/1992 | Scharf |
| 5,154,611 A | 10/1992 | Calvin |
| 5,156,290 A | 10/1992 | Rodrigues |
| 5,160,077 A | 11/1992 | Sticklin |
| 5,172,810 A | 12/1992 | Brewer |
| 5,199,567 A | 4/1993 | Discko, Jr. |
| 5,217,663 A | 6/1993 | Seville |
| 5,219,525 A | 6/1993 | Harrison |
| 5,246,105 A | 9/1993 | Eykmann et al. |
| 5,249,963 A | 10/1993 | McGarrigle |
| D341,909 S | 11/1993 | Schneider |
| 5,257,721 A | 11/1993 | Smith et al. |
| 5,282,563 A | 2/1994 | Oliver et al. |
| 5,340,550 A | 8/1994 | Johnsen et al. |
| 5,358,112 A | 10/1994 | Gardner |
| 5,368,482 A | 11/1994 | Johnsen et al. |
| 5,369,902 A | 12/1994 | Minster |
| 5,372,252 A | 12/1994 | Alexander |
| 5,377,823 A | 1/1995 | Steen et al. |
| D355,105 S | 2/1995 | Nemazi |
| D356,655 S | 3/1995 | Maniago |
| 5,456,361 A | 10/1995 | Walsh et al. |
| D366,537 S | 1/1996 | Johnsen et al. |
| 5,525,314 A | 6/1996 | Hurson |
| 5,538,421 A | 7/1996 | Aspel |
| 5,629,527 A | 5/1997 | Levitt et al. |
| D381,694 S | 7/1997 | Morgan |
| 5,645,206 A | 7/1997 | Ippisch |
| 5,647,746 A | 7/1997 | Chipman |
| 5,716,584 A | 2/1998 | Baker et al. |
| D392,433 S | 3/1998 | Norris |
| 5,749,730 A | 5/1998 | Johnsen et al. |
| RE36,072 E | 2/1999 | Uy |
| 5,913,422 A | 6/1999 | Cote et al. |
| 5,938,438 A | 8/1999 | Chipman et al. |
| 5,967,778 A | 10/1999 | Riitano |
| 5,989,699 A | 11/1999 | Kuczynski et al. |
| 6,036,490 A | 3/2000 | Johnsen et al. |
| 6,257,888 B1 | 7/2001 | Barham |
| 6,322,363 B1 | 11/2001 | Beecher et al. |
| 6,325,968 B1 | 12/2001 | Fricker et al. |
| D457,731 S | 5/2002 | Isaac |
| 6,436,351 B1 | 8/2002 | Gubernator et al. |
| 6,464,497 B2 | 10/2002 | Landoz |
| 6,485,822 B1 | 11/2002 | Osiecki et al. |
| 6,564,490 B1 | 5/2003 | Avila |
| 6,592,280 B2 | 7/2003 | Petrich et al. |
| 6,681,925 B2 | 1/2004 | Fischer et al. |
| 6,687,925 B2 | 2/2004 | Minnick |
| 6,719,560 B2 | 4/2004 | Capt |
| 6,722,067 B1 | 4/2004 | Kennedy et al. |
| 6,742,659 B2 | 6/2004 | Clark et al. |
| 6,776,616 B2 | 8/2004 | Dryer |
| 6,890,115 B2 | 5/2005 | Le Moing |
| D588,766 S | 3/2009 | Dunshee et al. |

(56) References Cited

U.S. PATENT DOCUMENTS

| | | |
|---|---|---|
| 7,763,038 B2 | 7/2010 | O'Brien |
| D659,837 S | 5/2012 | Oien et al. |
| 8,230,994 B2 | 7/2012 | Johnsen et al. |
| 8,231,734 B2 | 7/2012 | Johnsen et al. |
| 8,696,820 B2 * | 4/2014 | Vaillancourt .......... A46B 9/005 134/32 |
| 2001/0035384 A1 | 11/2001 | Davis et al. |
| 2002/0106609 A1 | 8/2002 | Palermo et al. |
| 2003/0039942 A1 | 2/2003 | Phillips |
| 2004/0068820 A1 | 4/2004 | Johnsen et al. |
| 2004/0139642 A1 | 7/2004 | Johnsen et al. |
| 2006/0019217 A1 | 1/2006 | Yates |
| 2006/0166170 A1 | 7/2006 | Masters |
| 2006/0270747 A1 | 11/2006 | Griggs |
| 2007/0205124 A1 | 9/2007 | Johnsen et al. |
| 2008/0311543 A1 | 12/2008 | Viscomi et al. |
| 2009/0136896 A1 | 5/2009 | Shuster |
| 2011/0068031 A1 | 3/2011 | Johnsen et al. |
| 2011/0229843 A1 | 9/2011 | Oien et al. |
| 2012/0003605 A1 | 1/2012 | Johnsen et al. |

OTHER PUBLICATIONS

"A Guideline for the Safe of Autoclaves", University of Ottawa, Environment Health and Safety Service, Jul. 9, 2003, http://www.uottawa.ca/services/ehhs/autoclave.pdf, 26 pages.

U.S. Appl. No. 10/684,344, filed Oct. 10, 2003, Johnsen et al.

U.S. Appl. No. 13/562,110, filed Jul. 30, 2012, Johnsen et al.

U.S. Appl. No. 29/428,599, filed Aug. 1, 2012, Oien et al.

Jordco, Inc., Jordco E-Foam, Copyright 2000-2011, Retrieved on Oct. 26, 2011, http://www.jordco.com/efoam.html, 1 page.

U.S. Patent and Trademark Office, Office action regarding U.S. Appl. No. 12/726,208, Dec. 1, 2014, 13 pages.

Dec. 24, 2012, International Search Report from The U.S. Receiving Office in PCT/US2012/53529, which is The international application to this U.S. application.

Dec. 24, 2012, Written Opinion of the International Searching Authority from the U.S. Receiving Office in PCT/US2012/53529, which is The international application to this U.S. application.

\* cited by examiner

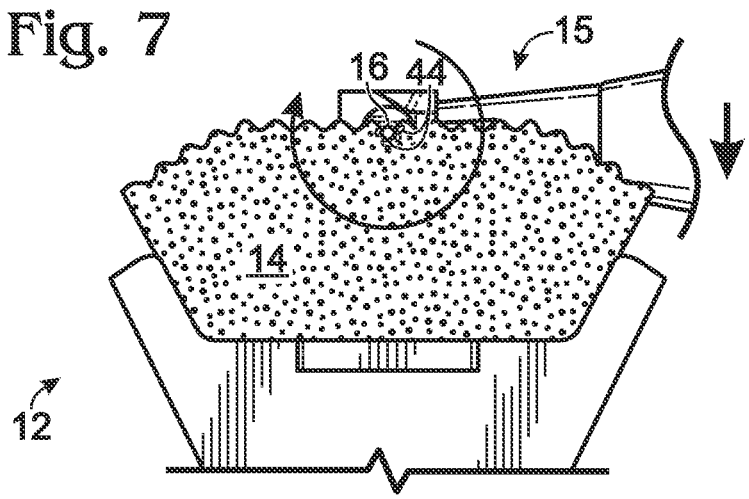

METHOD AND APPARATUS FOR CLEANING AND STORING ENDODONTIC TOOLS

CROSS-REFERENCE TO RELATED APPLICATIONS

This application claims priority to U.S. Provisional Patent Application Ser. Nos. 61/529,653 filed Aug. 31, 2011 and 61/695,227 filed Aug. 30, 2012, both of which are hereby incorporated by reference. This application also incorporates by reference in its entirety U.S. Pat. No. 8,231,734.

INTRODUCTION

Various industries use different types of instruments. In some industries, the instruments may need to be maintained in a substantially clean state during use. However, use of the instruments may expose the instruments to different types of contaminants, including bio-contaminants, dust, dirt, grime, etc. It may be desired to quickly and effectively reduce the level of contaminants on the instruments prior to, during or after use. For example, in the medical and/or dental fields, instruments may need to be cleaned prior, during, and after medical and/or dental procedures.

As an example, dental instruments may require periodic servicing during a dental maintenance and/or treatment procedure, such as an endodontic procedure. During an endodontic cleaning procedure of a root canal, the endodontic instruments may collect various contaminants, such as dentin shavings, pulp tissue, canal debris, bacteria, biofilms, and/or various medicaments. It is important for dentists to continually clean their instruments of such materials to avoid reintroducing debris back into a canal. It is also important to keep the instruments clean to improve the shaping or cleaning capacity of the instrument.

In an endodontic procedure, dentists must also have continued, ready access to instruments, such as endodontic instruments (also referred to as files). The endodontic instruments may be used to gauge the depth of root canals prepared in a patient's teeth. Typically, a dental assistant is employed to hold an instrument dispenser from which the dentist can withdraw sterile endodontic instruments.

Until about 2000, dentists could routinely perform endodontic cleaning and shaping of root canals by using stainless steel hand (also referred to as stationery) instruments. A hand instrument is very similar in appearance to a miniature drill bit, but the non-working end has a very small plastic handle to serve as a finger grip. These instruments graduate in size from a tip diameter as small as about 0.06 mm upwards to about 1.20 mm. They have very little taper to them and require manual hand and finger manipulation. These non-rotating (i.e., "stationery") instruments were typically inserted into a root canal and with one's fingers manually advanced into the canal using an action similar to winding a watch. This action serves to scrape the canal wall and thereby enlarge and shape it. Along with this shaping action, it is also serves to clean the canal walls by removing the pulp, microorganisms, debris and other contaminants. These instruments are still used by dentists today, but in a much different and reduced role.

One way to clean contaminants from the endodontic instruments required wiping the instruments with a gauze sponge. Wiping the instrument with such a sponge may be inadequate to clean the instruments and may be cumbersome.

Another way to clean contaminants from the endodontic instruments involved wiping the instruments on a foam cushion or inserting the instruments into a foam cushion designed to capture the instrument and clean this material off. Typically the cleaning is accomplished by inserting an instrument into the foam cushion with an in and out stabbing action to clean the debris off the instruments. Removal of the instrument after stabbing will leave the contaminant behind in the foam cushion. One such cushion for use in this method was disclosed in U.S. Pat. No. 8,231,734, which is hereby incorporated by reference. One such cushion is identified commercially as the JORDCO® E-FOAM® foam. The cushion of the '734 patent for this purpose was disclosed to have a recommended 25% indentation force deflection (IFD) within a range of 80.00 to 120.00 pounds force (identified as N in the '734 patent but where units are pounds force) and a density in the range of 20 kg/m$^3$ to 30 kg/m$^3$.

Around 2000, a new revolution in endodontic root canal therapy emerged. With the improvement in metallurgy, instruments started to appear constructed of a nickel-titanium alloy. The alloy was selected for having incredible flexibility and memory, which allows the instrument to be safely passed through a canal with great safety and efficiency. Early versions were supplied as hand instruments, but soon after they were made to fit a motor driven rotary dental hand drill. It soon became obvious that with proper training a dentist could experience superb results with this new "rotary" root canal therapy technique. Examples of rotary instruments for insertion into a dental hand drill include the GT .30-.06 and the Profile .775-.06, both by DENTSPLY® Tulsa Dental. Of course, maintaining clean rotary instruments is equally as important as maintaining clean stationery instruments.

SUMMARY

One or more embodiments of the present disclosure may include methods and systems for cleaning and/or storing instruments. In an embodiment of the present disclosure, an endodontic instrument servicing system may comprise a socket-forming member that may include spaced wall members that define a socket. An at least partially open-cell foam body may be secured within the socket that is configured for cleaning contaminated instruments. The body may have an indentation force deflection greater than 120 pounds force (lbf) and be configured to substantially grip a rotating contaminated instrument in contact with the body without tearing the foam body.

BRIEF DESCRIPTION OF THE DRAWINGS

FIG. 7 is a schematic illustration of the use of the cushion shown in FIG. 1 to clean a rotating instrument in an embodiment of a cleaning method of the present disclosure.

DETAILED DESCRIPTION

As disclosed herein, a porous material is provided that enables storing and/or cleaning of instruments, including rotary and stationary instruments. The porous material may be used to clean instruments from a variety of industries, including, but not limited to, high-technology industries, medical industries, dental industries, etc. Recently, it has been discovered that a superior way of cleaning some tools, such as endodontic tools, involves inserting the tool into a foam material, rotating the file tool, then withdrawing the tool from the foam and/or rotating the file when depressed horizontally onto the top of the foam and then withdrawing the file from the top of the foam. However, prior foam products, such as the foam disclosed in U.S. Pat. No. 8,231,734, failed in this procedure because the foam breaks down and tears, leaving undesired and unacceptable dental debris and torn foam material on the file when it is withdrawn from the foam. Recent studies have surprisingly demonstrated that foam materials having higher density and force deflection specifications yield improved cleaning functionality when used in a procedure with a rotary file apparatus. This higher density foam can also still be used for storage of tools by having tools inserted therein.

Although the following description illustrates the use of a porous material in a dental instrument servicing system, it should be appreciated that a similar porous material may be used alone or in other types of servicing systems, such as medical, dental and high-technology instrument servicing systems. For illustration purposes, the porous material may be mounted in such dental instrument servicing systems described and disclosed in U.S. Pat. Nos. 4,280,808, 5,368, 482, 6,036,490, and 8,230,994; and U.S. Patent Application No. 2011/0229843, all of the disclosures of which are hereby incorporated by reference. Each of those servicing systems includes a holder and cushion for insertion into the holder. A cushion having the characteristics of the present disclosure may be used in replacement of the prior art cushion described in those systems, as used in accordance with the methods and systems of the present disclosure, as described in more detail below.

Figure 1:
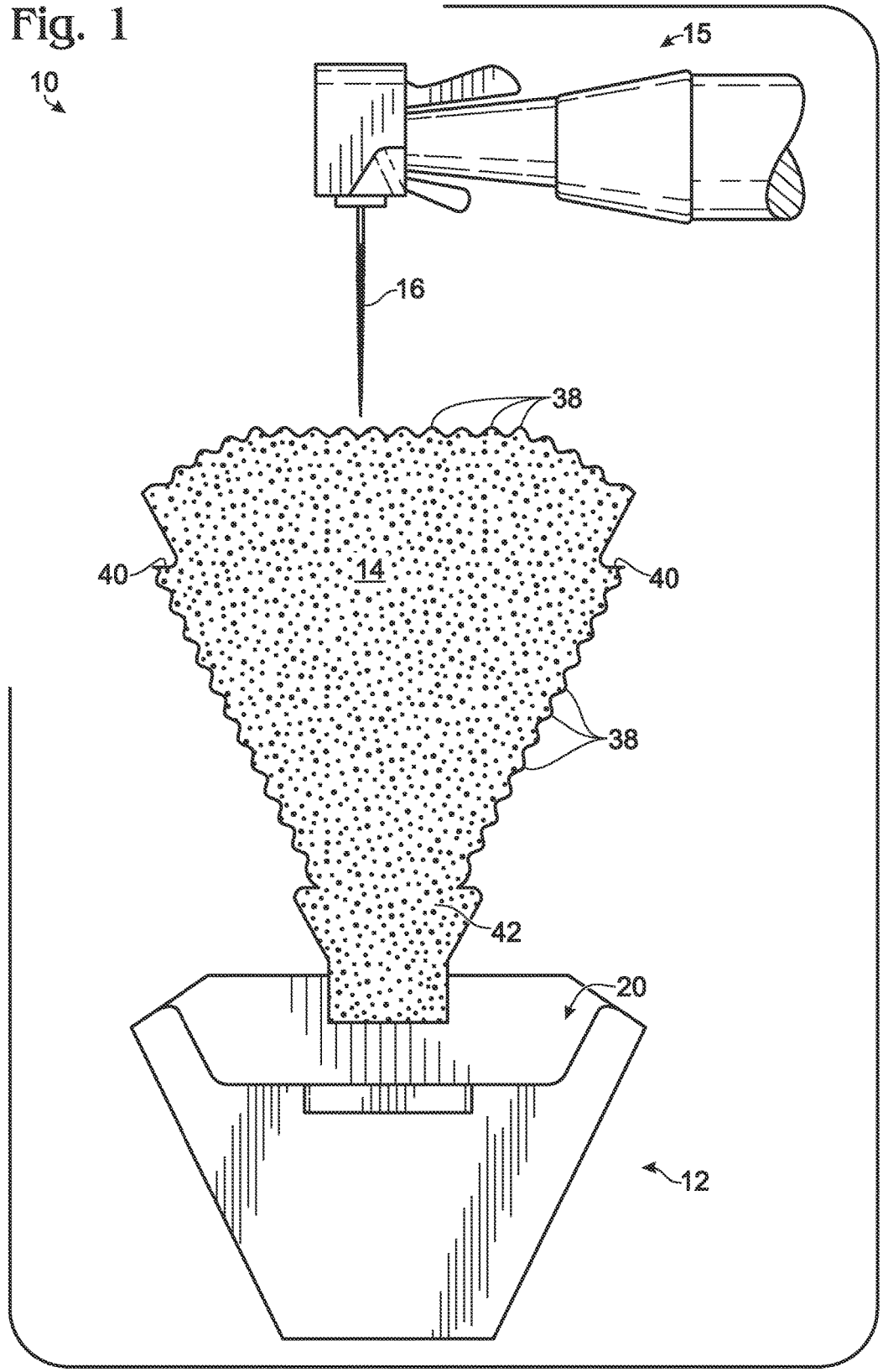
FIG. 1 is a schematic view of an embodiment of the present disclosure of a dental instrument servicing system including a holder and a cushion configured to receive a rotary tip or flute portion of a drill.

Referring to FIG. 1, an exemplary dental instrument servicing system 10 is generally shown that may include a socket-forming member or holder 12 configured to carry an insert or cushion 14, and a rotary dental drill 15 having a rotary tip (or file or instrument or flute) 16 that is insertable into cushion 14. The system may further include a finger mount 18 and a medicament holder 19 (see FIG. 2). Cushion 14, finger mount 18, and medicament holder 19 may be selectively removable from the socket-forming member.

Socket-forming member 12 may be any device configured for holding a cushion. Although not required, the socket-defining member may be of unitary construction, being formed of a lightweight material such as plastic or aluminum. These materials, it will be appreciated, typically are inexpensive, may be formed by molding processes, and may be suitable for hand-worn use.

Figure 2:
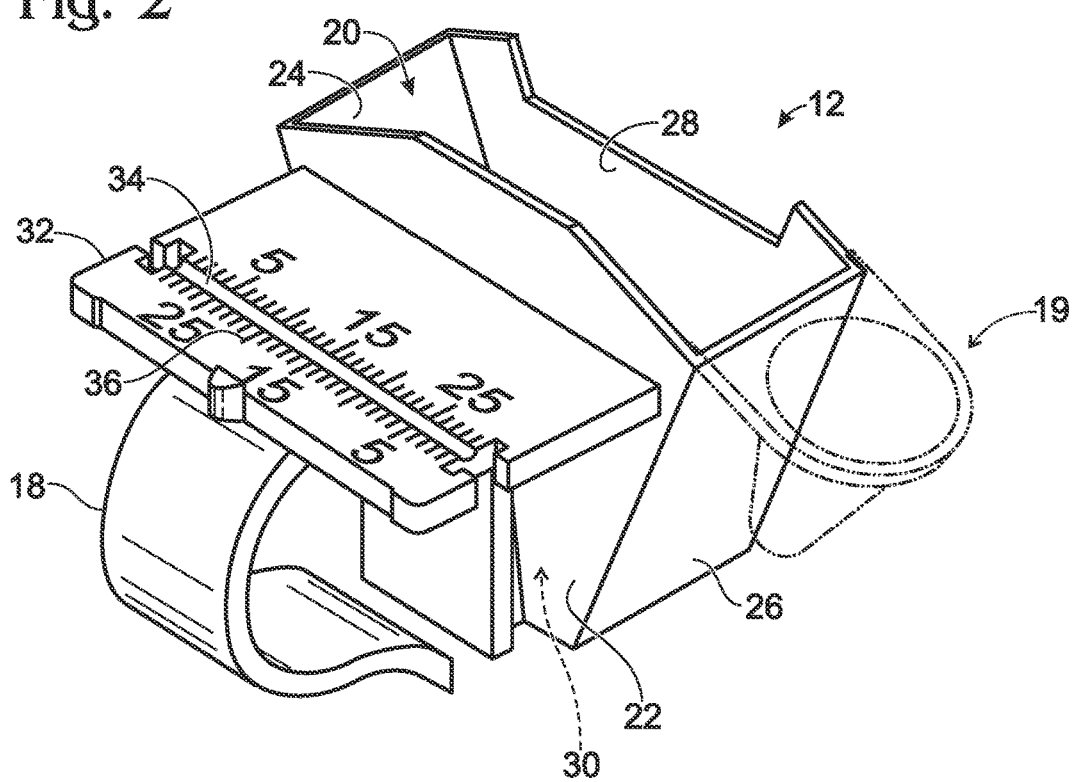
FIG. 2 is an isometric view of an embodiment of the present disclosure of a holder configured to hold a cushion.

In an embodiment shown in FIG. 2, socket-forming member 12 may include plural walls that define a passage or socket 20. Socket-forming member 12 may define a double-open-ended socket 20, which provides a seat for cushion 14. For example, front wall 22, side walls 24, 26, and back wall 28 may form passage or socket 20. In some embodiments, cushion 14 may be removably inserted into socket 20, retained by one or more of the walls of socket forming member 12. Cushion 14 may be somewhat abrasive and/or have a relatively rough surface such that the abrasiveness and/or surface of the cushion may be frictionally retained within passage 20. The member may include one or more passages configured to carry one or more cushions, as desired.

Figure 3:
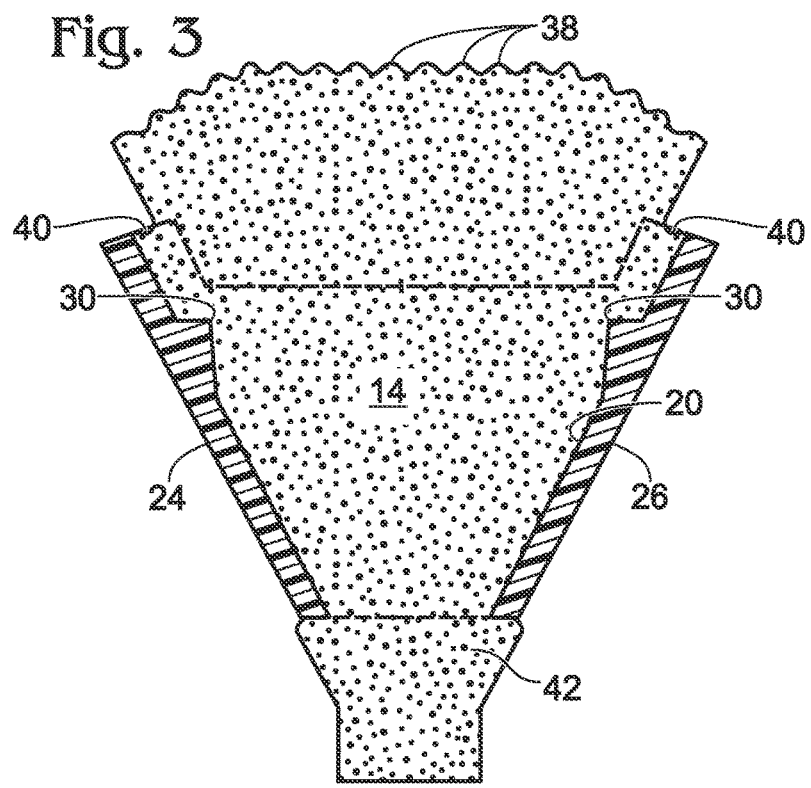
FIG. 3 is a section view of the holder of FIG. 2 showing internal protrusions gripping an inserted cushion.

In some embodiments, the frictional engagement between cushion 14 and the walls of passage 20 may be enhanced by the provision of one or more projections 30 disposed on the interior surface of one or more of the walls of the socket 20 (see FIG. 3).

As shown in FIG. 2, finger mount 18 may be attached to socket-forming member 12 and may allow the system to be positioned on an individual's forefinger for use during a dental procedure. The finger mount may be removably attached to socket-forming member 12 via a cooperative slide arrangement, as described in previously issued U.S. Pat. No. 4,280,808 and US Application No. 2011/0229843, each of which have been incorporated by reference above. Typically, such a system is relatively lightweight and is not appreciably more burdensome than a large ring. Thus, such a system typically will not significantly interfere with use of the wearer's hand.

Socket-forming member 12 also may include an outwardly projecting shelf 32. Shelf 32 may extend outward covering finger mount 18 and may protect a user's finger from injury by sharp instruments, such as endodontic files, which may be inserted into cushion 14. The shelf may further serve as a measuring device for use in connection with endodontic files. Thus, shelf 32 may include a trough 34 for receipt of endodontic files. A scale 36 may be etched into shelf 34, accommodating accurate positioning of depth markers on the file.

Medicament holder 19 may be removably applied to socket-forming member 12. Medicament holder 19 may include a cup section configured to hold a medicament in a dosage container and a clip section (not shown) configured to selectively attach the medicament holder to the socket-forming member.

The socket-forming member may include other features, such as a service platform (not shown) adapted for receipt of depth markers.

FIGS. 1 and 3 illustrate an example of structural features of cushion 14. Cushion 14 may be formed of a porous material, such as foam, suitable for use in holding and cleaning instruments, such as endodontic files. Cushion 14 may also include characteristics configured to not grab, tear, or shred foam while instrument 16 is in contact with cushion 14 while rotating.

Cushion 14 may include a surface configured to enable an instrument to be inserted into the body of the cushion. Stationery and rotary instruments, such as rotary tip 16, may puncture the surface and be pushed into an interior region of the cushion (see middle panel of FIG. 6, for example). The foam may be configured to enable instruments of varying shaft diameters and lengths to easily penetrate cushion 14. The surface of cushion 14 may be resilient, such that the surface is able to recover from the puncture and return to its prior state. The cushions may be described as "crisp" or "firm" such that the tip of an instrument (e.g., instrument 16) easily pierces the surface of cushion 14. Such cushions may adequately resist collapsing when penetrated by an instrument. Materials that collapse or resist the penetration of files or other instruments may frustrate the user and are therefore considered unsatisfactory.

Cushion 14 may be generally pie-shaped such that it conforms closely to the shape of the socket. However, it should be appreciated that cushion 14 may be any suitable shape depending on the system. Cushion 14 may be adapted to receive files of a predetermined size and/or style. Therefore, the system may be used to organize endodontic files, or other instruments, by placement of selected files into the cushion and/or to clean instruments, including rotary and stationary instruments, using the cushions, as will be described in more detail below.

A peripheral surface of cushion 14 may include a plurality of ridges or corrugations 38 that may enhance the retention of cushion 14 within passage 20 of member 12. The corrugations may increase and/or enhance the frictional engagement between the peripheral surface of the cushion and the interior surfaces of side walls 24, 26 and/or projections 30. Ridges or corrugations 38 may be rounded or they may include a plurality of angularly intersecting flat surfaces that may provide a stepped or saw tooth configuration, or any other configuration desired.

In some embodiments, cushion 14 may include one or more features to ensure proper seating in socket 12. Proper seating may allow for providing a specific desired density of cushion 14 and/or placement of cushion 14 in socket 12. For example, the specific foam shape and/or contour may ensure proper seating.

Cushion 14 may also include one or more ledges or seating shoulders 40 that may align with a top surface of socket 14 or a seating shoulder indicator of socket 12. Ledges 40 may aid in proper positioning of cushion 14 in socket 12.

Cushion 14 may also include a bulbous bottom or insertion tip 42 configured to be pulled through an open bottom end of socket 12. When pulled through, bulbous bottom 42 may decompress and expand to a size that is larger than the open bottom end, thereby helping to secure cushion 14 into socket 12 in a desired seated position. Precise and proper positioning of cushion 14 in holder 12 may keep the foam density of cushion 14 precisely consistent so that files can be cleaned. For example, when tip 42 is pulled through the bottom of holder 12, cushion 14 may lock into place in holder 12. This may allow for the foam to have consistently the same desired density each and every time it is seated in holder 12.

Cushion 14 and socket 12 may include control features to ensure proper seating of cushion 14 in socket 12. For example, cushion 14 may include tapered features that specifically seat into reciprocal tapered features in socket 12 to provide the desired seating. Cushion 14 may have a tapered seating feature on the insertion end to assure precise mounting and density of the polyurethane open cell foam when in socket 12. Cushion 14 may have a tapered seating feature on the wider terminal end to assure precise mounting and density of the polyurethane open cell foam when in socket 12.

As best seen in FIGS. 2 and 3, passage 20 may be shaped as a tapered longitudinal channel. The tapered channel may provide a superior top working surface for cushion 14, allowing for organizing, cleaning and transferring endodontic instruments and to control the precise positioning of cushion 14 in socket 12. The tapered channel may provide predictable compression of cushion 14 while generating retention forces that stabilize cushion 14 in socket 12.

Cushion 14 may have one or more raised features on each side that seat within reciprocal features of socket 12 to assure precise mounting and density of the polyurethane open cell foam when in socket 12. The control feature may include a plurality of bilateral solid tapered indentations.

In some embodiments, cushion 14 may be configured as part of a handheld or stand alone device. The socket-forming member, for example, may be configured as a handheld or stand-alone device. The cushion may be hard surface mounted. The cushion may take any shape or form desired.

Cleaning of Rotating Instruments.

The characteristics of a porous material, such as cushion 14, are configured to allow for cleaning of a rotary instrument that is rotating while in contact with the porous material. The reason for contacting a rotating file with the porous material is to aid in the removal of contaminants from the file in an easy manner. A file cleaned by such a method, however, should have the contaminants removed and also not have any foam or other residue on the file after the cleaning. There are several ways a user may clean a rotating file using the porous material, including where a user may insert the rotating file into the cushion and/or where a user may depress the rotating file horizontally against an outside surface of the cushion. The characteristics of the porous material must be able to withstand these different types of cleaning methods of rotating instruments while not tearing, grabbing, or shredding from the rotation of the instrument, which would leave undesired foam, contaminants or other residue on the file, thus frustrating the overall cleaning objective.

Failure of Prior Art Cushion Characteristics

While rotary instruments have become commonplace in endodontic practice, the prior art cushions have failed to allow for successful cleaning of such instruments when the instrument is contacted with the foam while rotating. It has been found that the characteristics of the prior art porous material, such as the cushion designed for cleaning the stationary instruments, could not withstand contact with a rotating instrument without tearing, grabbing, and/or shredding of the cushion, hence leaving undesired torn off foam on the tip after the removal of the tip from the prior art cushion.

Figure 4:
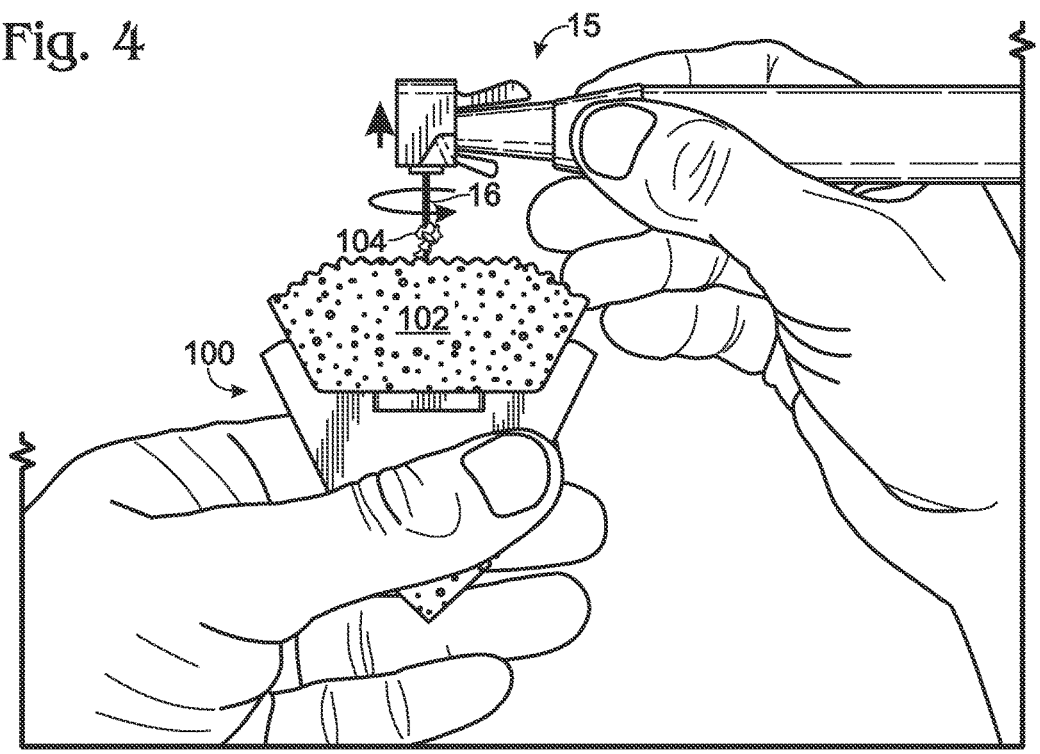
FIG. 4 is a front view of a cushion having characteristics found in the prior art, illustrating where a rotary tip of a dental drill has torn and grabbed a portion of the cushion after being rotated in contact with the cushion.

For example, as illustrated in FIG. 4, it has been found that insertion of a rotating instrument into the prior art cushions disclosed in U.S. Pat. No. 8,231,734 (one such cushion is identified commercially as the JORDCO® E-FOAM® foam) tends to cause snagging as the file occasionally grabs onto the cell structure of the low density cushion. This often results in grabbing, tearing and/or shredding of the foam. For example, FIG. 4 shows a socket 100 holding a prior art cushion 102 and a rotating tip 16 attached to a drill 15 (the rotation motion is shown by the circular arrow) being removed upwards from prior art cushion 102. Torn off portions 104 of the prior art cushion 102 remain on tip 16 upon removal, which is undesired and unacceptable.

Likewise, a similar issue resulted from pressing a rotating file horizontally against the top surface of a prior art cushion by applying a slight amount of pressure during the cleaning procedure. The rotating file was slowly dragged or swiped on the foam horizontally during this procedure, causing the cushion to grab the file and in some cases to tear and/or shred the foam. Torn off portions of the prior art cushion remain on the tip upon removal, which is undesired and unacceptable.

The above results of the prior art cushion were also confirmed by testing the cleaning of two types of rotary files, a GT.30-.06 (DENTSPLY® Tulsa Dental) and a Profile .775-.06 (DENTSPLY® Tulsa Dental). Both were tested in rotary tests where the files while rotating were placed in contact with the prior art JORDCO® E-FOAM® cushion. The cushion had a 25% indentation force deflection (IFD) of around 104 pounds force, along with a density, air flow and cell count, all within the range disclosed in U.S. Pat. No. 8,231,734 (N was meant as pounds force in the '734 patent). During the testing, each file was mounted and tested using an electric motor hand piece set to a speed of 320 rpm. A test piece of foam was mounted and fully seated into an ENDORING® II cup. In one test, each rotating file was inserted or stabbed three times into the top faceted surface of the foam insert. The foam was observed for any grabbing, tearing or shredding. In the second part of the test, each rotating file was drawn horizontally across the top faceted surface of the foam insert with a slight pressure applied to the file to simulate a cleaning action. The results of the study were dramatic in that the tests yielded a grabbing, tearing and/or shredding of the foam being studied when a moving rotary file was inserted into or removed from the foam or drawn across the top surface of the foam in a horizontal fashion. This left undesired torn off portions of the cushion on the file after the cleaning procedure was completed. Based on this, the prior art cushion could not be predictably used to clean rotating files without the risk of grabbing, tearing and/or shredding of the cushion using these two techniques.

Hence, there exists a need for a cushion insert having characteristics that allow for cleaning of instruments in contact with the foam while rotating or moving, but without snagging, tearing, grabbing, or shredding of the foam.

Characteristics of the Porous Material of the Present Disclosure

The characteristics of the foam of the present disclosure have yielded surprisingly beneficial results in solving the issues with the prior art cushions for cleaning instruments rotating in contact with the cushions. Tests have been conducted to determine the suitable characteristics/composition for cushion 14 to overcome the issues of the prior art. An exemplary foam which has been used successfully to clean rotary files is described in TABLE 1 below:

TABLE 1

Characteristics of Porous Material/Cushion of the Present Disclosure

| Density | |
| --- | --- |
| (pounds per cubic foot) or | 1.5-3.0 lbs/ft$^3$ |
| (kilograms per cubic meter) | 24.1-48.1 kg/m$^3$ |
| Material Cell Count | 12-20 cells/cm |
| (cells per centimeter) | |
| Air Flow | |
| (cubic feet per minute) or | 0.1-5.0 ft$^3$/min |
| (cubic decimeters per second) | 0.05-2.4 dm$^3$/sec |
| 25% IFD Indentation Force Deflection | 121-198 lbf |
| (pounds force) | |

It should be appreciated that although an exemplary foam is described in detail, the composition of suitable cushions may vary. For example, suitable foams for use in the present disclosure may have a different density, air flow, 25% indentation force deflection (IFD), compression force deflection (CFD), cubic feet per meter (CFM) rate, cell count, etc. Other characteristics, such as the compression force deflection (CFD), and/or tensile and/or tearing strength of a foam may also be considered. The foam characteristics, as described above, are included only for illustrative purposes and are not intended to include all suitable compositions for cushion 14.

Generally, the foam characteristics may be balanced to achieve a suitable material for use in insertion and/or rotary cleaning of instruments. Selection of one or more of the density, material, and/or cell count of the foam may effect a change in the air flow, the indentation force deflection, the density, the compression force deflection, or other characteristics of the cushion. For example, selection of the appropriate material may include balancing the density and cell count of the foam, such that the foam functions as desired.

The "firmness" of the cushions may be measured using the 25% indentation force deflection (IFD) test according to the standard ASTM D 3574 Test B1: Specified Deflection. An IFD number represents the force required to indent a foam sample by a specified percentage (e.g. 25%) of its original thickness. As shown in TABLE 1 above, suitable foams have a 25% indentation force deflection of approximately 121 lbf to 198 lbf.

It further should be noted that the foam within the cushions may be described in relation to their cubic feet per minute (CFM) values. CFM values may be obtained by determining the cubic feet per minute air flow through a standard 15×15×4" thick test piece of foam used in the IFD tests. As shown in TABLE 1 above, suitable foams have a CFM value of 0.1 ft$^3$/min to 5.0 ft$^3$/min (or 0.05 dm$^3$/sec to 2.4 dm$^3$/sec). Foams with other CFD values may be suitable as well.

In some embodiments, the cushion may be composed of polyurethane and/or urethane. The cushion may be composed of, and/or include, melamine. The cushion may comprise and/or be made from other types of materials, such as rubber, polyester, polyether, etc.

Polyurethane and/or urethane cushions may be able to withstand steam autoclaving without substantially deforming, melting, or producing any noxious out-gassing of toxic substances during the steam autoclaving process. Moreover, polyurethane is widely and safely used in many medical and dental applications.

As briefly noted above, in some embodiments, it may be desirable to sterilize the cushions (and the instruments) prior to use. For example, in many environments, steam autoclaving may be used to sterilize the cushions. Thus, the cushions may be configured to withstand sterilization via steam autoclaving prior to use. Due to the use of the cushions in medical and dental applications, the cushions typically may be configured to withstand steam autoclaving as performed in clinical environments, where the steam autoclaves typically operate within a range of between 275 degrees and 300 degrees Fahrenheit and a range of between 20 psi and 30 psi.

The cushions may include an at least partially open-cell foam body. The at least partially open-cell body may allow steam from an autoclave to penetrate an interior region of the cushion. Penetration of the interior region enables steam to surround and effectively sterilize endodontic files or other instruments at least partially disposed within the cushion. Typically, substantially closed cell structures prevent steam from passing into the interior region of the cushion. Such closed cell cushions may not provide the necessary sterilization of the instruments positioned within the cushion. In contrast, cushions that have an air flow of more than approximately 1.0 dm$^3$/second (as measured according to the standard ASTM D 3574 Air Flow Test G) may be adequate to enable sterilization of endodontic files positioned in the interior region of the cushion. As shown in TABLE 1, the cushions have an air flow of about 0.05 dm³/second to about 2.4 dm³/second.

Figure 5:
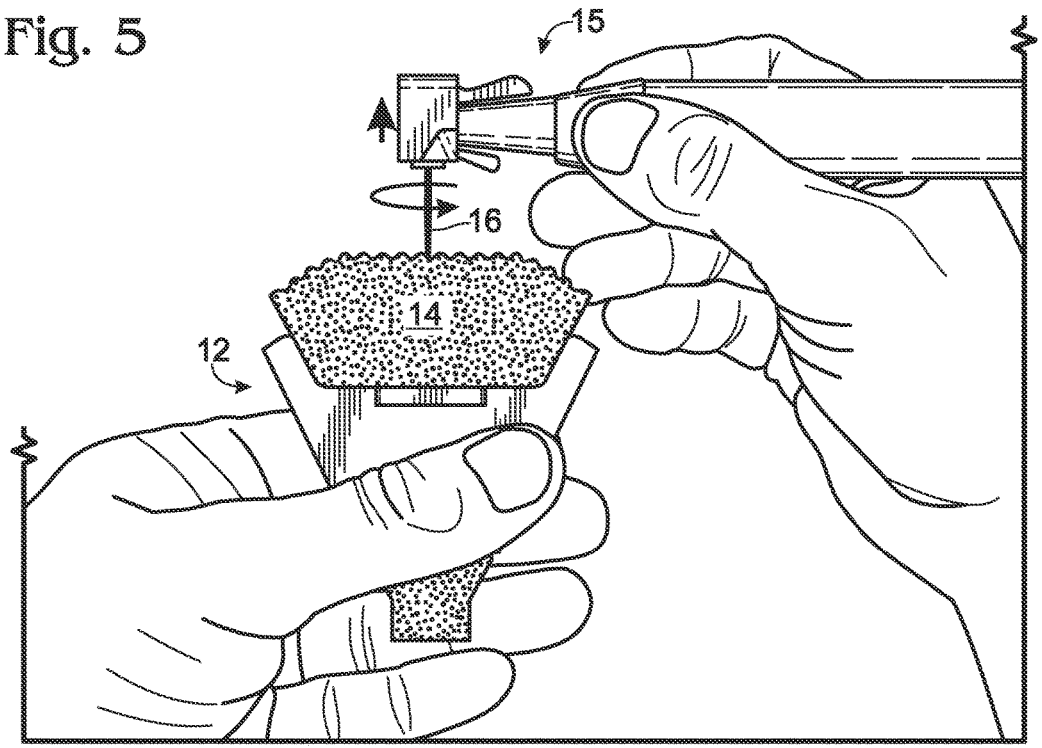
FIG. 5. is a front view of a cushion of the present disclosure, illustrating where a rotary tip of a dental drill has not torn and grabbed a portion of the cushion after being rotated in contact with the cushion.

Here, the cushion characteristics of the present disclosure have solved the grabbing, tearing and/or shredding problem found when contacting the prior art cushions with a rotating instrument for cleaning. For example, this is illustrated in FIG. 5, which shows that tip 16 of drill 15 lacks the torn off portions 104 after being rotated in contact with cushion 14 and withdrawn from cushion 14. Cushion 14 may include some, all, or a combination of one or more of the following characteristics: a polyurethane open cell foam with an IFD range of 121-198 lbf, and/or a weight density range of 24.1-48.1 kg/m³, and/or an air flow In the range of 0.05-2.4 dm³/second and/or any other characteristics disclosed in TABLE 1, used to clean and store endodontic instruments, which may include rotary and/or hand endodontic instruments.

Figure 6:
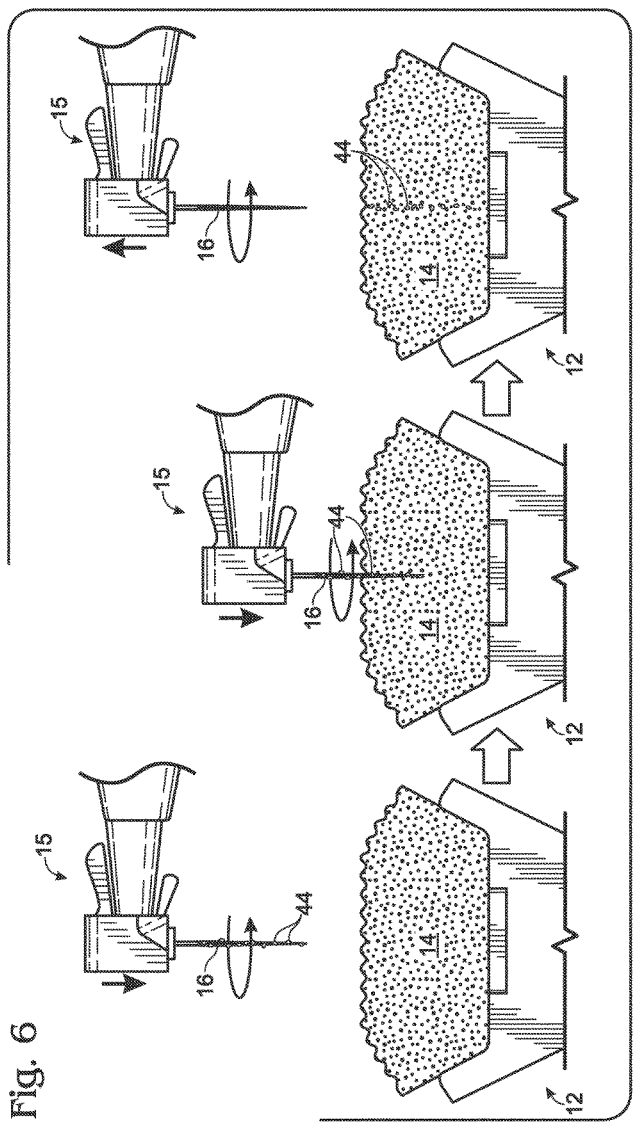
FIG. 6 is a schematic illustration of the use of the cushion shown in FIG. 1 to clean a rotating instrument in an embodiment of a cleaning method of the present disclosure.

FIG. 6 schematically illustrates the instrument cleaning properties of cushion 14. Generally, the abrasive action of the foam in a cushion functions to substantially clean instruments inserted therein. More specifically, the porous material in the cushion is configured to grip an instrument, such as a dental instrument attached to a rotary drill (indicated generally as instrument 16 and drill 15 in FIG. 6). The gripping characteristics of the porous material substantially retains contaminants and other residuals from the instrument.

For example, during a medical or dental procedure, an instrument may accumulate contaminants (also referred to as bioburdens) 44 that may cling to the file. For example, as shown in the left panel of FIG. 6, contaminants 44 may extend along the shaft of instrument 16. Insertion of instrument 16 into cushion 14 may occur by penetrating the surface of cushion 14, as indicated by the downward arrow in the left panel. Drill 15 may be rotating file 16 before penetrating the surface. Drill 15 may initiate rotation of file 16 after penetrating the surface.

The middle panel of FIG. 6 illustrates entry of instrument 16 into an interior region of cushion 14. Contaminants 44 may be sloughed off of shaft 16 as shaft 16 rotates in the cushion 14. The cells within the cushion are configured to substantially grip the file as it is inserted into and pulled out of the cushion. In some embodiments, the drill may be rotating at a speed of 100-1000 rotations per minute (RPM), though characteristics of cushion 14 may accommodate cleaning instruments rotating at an RPM outside this range.

In some embodiments, further cleaning of instrument 16 may include the removal from and the reinsertion of shaft 16 to/into cushion 14, thereby repeating the steps illustrated generally in FIG. 6. Multiple insertions of the dental instrument into the cushion may function to substantially decrease the level of contaminants 42 on instrument 16. Hence, instrument 16 may be rotated in a first pass, then removed from cushion 14. Instrument or file 16 may then be re-inserted into cushion 14 and rotated again for another pass. One to five passes may be desirable for different applications to ensure the file is clean, though the file may be inserted for more passes as needed.

In some embodiments, instrument 16 is rotated in cushion 14 for about 1-3 seconds per pass. It is also possible to rotate for longer than 3 seconds, if needed. It is also possible to vary the time from pass to pass as desired.

In some embodiments, the rotational direction of drill 15 may be varied as desired. For example, drill 15 may rotate instrument 16 counterclockwise as shown in FIG. 6 before, during, and/or after the insertion and removal of instrument 16 from cushion 14. Drill 15 may rotate instrument 16 clockwise before, during, and/or after the insertion and/or removal of instrument 16 from cushion 14. Drill 15 may rotate instrument 16 with a mixture of counterclockwise and clockwise rotations as desired. Drill 15 may rotate instrument 16 counterclockwise during a first pass and then clockwise during a second pass, etc. as desired.

By gripping the instrument as it is rotating in a cushion, the contaminants may be displaced from the instrument to the cushion. The composition of the cushion will affect the removal of contaminants from the instrument. Specifically, a foam having the characteristics found in TABLE 1 above may significantly reduce contaminants on an instrument.

As is shown in the right panel of FIG. 6, removal of instrument 16 from cushion 14 results in contaminants 44 being left in cushion 14 as a result of the cleaning method. Shaft 16 may be free or substantially free of contaminants 44 and of torn off pieces of cushion 14 because cushion 14 was configured with characteristics such that cushion 14 would not tear, grab or shred upon contact with rotating instrument 16.

FIG. 7 illustrates an embodiment of a cleaning method where instrument 16 may be contacted to cushion 14 by depressing instrument 16 horizontally against the outer surface of cushion 14 rather than inserting instrument 16 into the interior surface of cushion 14. Instrument 16 may be rotated before, during, and/or after contact is made with cushion 14. As shown, instrument 16 is depressed between ridges 38 of cushion 14, but instrument 16 could also be depressed across ridges 38. The surface of cushion 14 could also be configured without ridges or in any formation desired. Instrument 16 could be depressed onto the surface in any way desired. Cushion 14 will grip and remove contaminents (such as contimanents 44) from cushion 14. Instrument 16 may be wiped on and/or swiped across the outer surface of cushion 14, and/or held in one position, during rotation of instrument 16 while depressed against cushion 14. Cushion 14 may have the characteristics described above that may allow cushion 14 not to tear, grab or shred upon contact with rotating instrument 16.

Instrument 16 may be rotated counterclockwise, clockwise, or a mixture of both directions, as desired, before, during, and/or after contact is made. Instrument 16 may be contacted with cushion 14 during rotation for 1 to 5 seconds, or for any length of time desired. Instrument 16 may be removed and re-depressed onto cushion 15 for 1 to 3 passes, or for as many passes as desired. The direction of rotation can be varied as desired during a pass and/or from pass to pass.

The method of inserting the instrument into the foam may be combined with the method of depressing the instrument horizontally against an outersurface of the foam as desired. One or the other could go first and then the method could be varied from pass to pass, such as by alternating if desired.

In some embodiments, a method may include providing a hand held polyurethane open cell foam with a 25% indentation force deflection (IFD) range of 121-198 lbf, and/or a weight density range of about 24.1-48.1 kg/m³, and/or an air flow in the range of about 0.05-2.4 dm³/sec used to clean and store endodontic instruments, which may include rotary and/or hand endodontic instruments, that cleans the rotating instrument by using a stabbing motion to pass the rotating instrument in and out of the polyurethane open cell foam one or multiple times. The method may include insertion of the instrument into the foam and/or depressing the foam horizontally against an exterior surface while instrument is rotating to clean the instrument.

Testing confirmed that using the insertion and depression methods with the cushions of the present disclosure did not result in grabbing, tearing, or shredding of the cushion by the rotating tips. Hence, the tips could be removed without foam portions remaining on the withdrawn file.

Testing also confirmed that contaminants can be successfully removed from the file to clean the rotating file using either the insertion or the depression method. Other testing also confirmed that a cleaning method involving inserting a rotating file into a cushion outperformed simply inserting a stationery file to clean. Other testing similarly confirmed that a cleaning method involving depressing a rotating file against the cushion outperformed depressing to wipe a stationery file across the cushion.

For example, the cushion of the present disclosure was found to clean more effectively than the prior art cushions using the traditional non-rotating stabbing method. A test was performed to gauge cleaning effectiveness, with the results illustrated in TABLE 2 below. Specifically, the cleaning effectiveness was measured using biological serial dilution techniques. Accordingly, the level of bioburdens (contaminants) on the instrument was measured prior to, and after insertion and removal (also referred to herein as a stab) of the instrument into and out of the cushion. As shown in TABLE 2 below, an 89.3% spore reduction level (level of bioburdens on the instrument) was achieved after a first stab of the instrument into the cushion of the present disclsoure. A second stab increased the spore reduction level to 95.6%. A 97.4% spore reduction level was achieved after three insertions (or stabs).

TABLE 2

| Foam | Cushion of the Present Disclosure | Prior Art Foam of U.S. Pat. No. 8,231,734 |
| --- | --- | --- |
| Spore Reduction: 1 Stab | 89.3% | 82.6% |
| Spore Reduction: 2 Stabs | 95.6% | 86.3% |
| Spore Reduction: 3 Stabs | 97.4% | 96.3% |

As is shown, the cushions of the present disclosure demonstrates improved spore removal compared to prior art cushions in the first two passes. The cushions of the present disclosure also demonstrate slightly improved performance with three stabs. The cushions of the present disclosure also removed almost as many spores in two stabs as the prior art cushion did in three stabs.

Other tests were performed to test the efficacy of the cushion of the present disclosure. For example, a test was performed to remove cement deposit from an instrument. The cement removal test mirrored the results of the spore removal test in that each pass with a given instrument provided better cleaning. All instruments passed the cleaning thresholds of the cement removal test with three stabs into foam of the present disclosure. Cushions having an IFD in the range of 161-173 lbf cleaned files in just two stabs. Cushions having an IFD of 156 lbf had one file clean in two stabs and one file clean in three stabs.

The cushions of the present disclose may provide several advantages over the prior art cushions. For example, the cleaning properties of a cushion in contact with a rotating instrument may be greatly enhanced because it takes less time to clean the instrument and contaminants are greatly removed while the instrument is moving in a rotary fashion in the cushion. This means the instrument may be cleaned without removing the rotary bit from the drill. Another advantage may be that rotating instruments that are vertically inserted in the cushion may not tear or shear the cushion, which nearly eliminates the chance of introducing cushion debris to an instrument and potentially introducing such debris back into the tooth. Another advantage may be that that the structural features of the cushion may help it load into and conform better to the socket-member. This may help eliminate the dislodgement during the use of loading and cleaning of all instruments, particularly rotary instruments, which may be due to the firmness and compressive pressure the inserted cushion exhibits against the walls of the cup. Another advantage may be that the cushion does not tear during horizontal cleaning as the cushion is much more tear resistant than prior art cushions, such as the prior art cushion. Another advantage may be that stationary or hand instruments may also be cleaned better using the cushion of the present disclosure.

Another advantage may relate to deformation as the cushion of the present disclosure may not deform under normal autoclave processing (heat) and thereby the loading and retention performance of the cushion as it is seated in the socket-member may not be compromised. In an autoclave the cushion of the present disclosure was stiff enough to resist significant deformation when placed under a load. The prior art cushion did not rebound.

In an embodiment of the present disclosure, a porous material, such as a foam cushion, is provided for insertion and/or rotary cleaning of instruments, including hand and rotary instruments. Such porous material may include an at least partially open-cell foam body and a surface. The porous material may be configured to substantially grip the instrument to remove a substantial portion of the contaminants from the instrument while the instrument is rotating and in contact with the porous material, but while not tearing, gripping, or shredding the porous material while rotating in contact with the porous material.

While the present description has been provided with reference to the foregoing embodiments, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring, nor excluding, two or more such elements.

What is claimed is:

1. An endodontic instrument servicing system, comprising:
   a socket-forming member including spaced wall members that define a socket; and
   an at least partially open-cell foam body secured within the socket configured for cleaning contaminated instruments, the foam body having an indentation force deflection (IFD) greater than 120 pounds force (lbf) and configured to grip a contaminated motor-driven instrument rotating at 100 to 1000 rotations per minute in contact with the foam body without tearing the foam body.

2. The system of claim 1, wherein the cell body is configured to reduce at least about ninety percent of bioburdens on the instrument after a single insertion of the instrument into the cushion.

3. The system of claim 1, further comprising a finger mount coupled to the socket-forming member to provide for attachment of the system to a user's hand.

4. The system of claim 1, wherein the body has an IFD within a range of 121 lbf to 198 lbf.

5. The system of claim 1, wherein the body has a cell count within a range of 12 cells/cm to 20 cells/cm.

6. The system of claim 1, wherein the body has an IFD within a range of approximately 156 lbf to approximately 173 lbf.

7. The system of claim 1, wherein the body has a density within a range of approximately 24.1 kg/m$^3$ to approximately 48.1 kg/m$^3$.

8. The system of claim 1, wherein the body has an airflow in a range of approximately 0.05 dm$^3$/sec to approximately 2.4 dm$^3$/sec.

9. The system of claim 1, wherein the body is comprised of polyurethane open-cell foam configured to receive a flute portion of a rotary file.

10. An instrument servicing system, comprising:

a handheld socket-forming member including a pair of spaced wall members that define a socket; and a resiliently deformable cushion for rotary insertion cleaning of instruments configured to be received within the socket-forming member, the cushion being an at least partially open-cell foam having an IFD within a range of 121 lbf to 198 lbf, an airflow in a range of 0.05 dm$^3$/sec to 2.4 dm$^3$/sec, a cell count within a range of 12 cells/cm to 20 cells/cm, and a density within a range of 24.1 kg/m$^3$ to 48.1 kg/m$^3$ the cushion being configured to grip a contaminated motor-driven instrument rotating at 100 to 1000 rotations per minute without tearing the cushion.

\* \* \* \* \*